(12) United States Patent
Rosenthal et al.

(10) Patent No.: US 6,559,655 B1
(45) Date of Patent: May 6, 2003

(54) SYSTEM AND METHOD FOR ANALYZING AGRICULTURAL PRODUCTS ON HARVESTING EQUIPMENT

(75) Inventors: Todd C. Rosenthal, Hagerstown, MD (US); Stuart W. Wrenn, Frederick, MD (US)

(73) Assignee: Zeltex, Inc., Hagerstown, MD (US)

( * ) Notice: Subject to any disclaimer, the term of this patent is extended or adjusted under 35 U.S.C. 154(b) by 0 days.

(21) Appl. No.: 09/844,698

(22) Filed: Apr. 30, 2001

(51) Int. Cl.[7] ................................................. G01J 3/28
(52) U.S. Cl. ....................................... 324/634; 250/252
(58) Field of Search ..................... 460/7, 149; 356/328; 324/634, 640, 644, 689; 250/252, 252.2, 339.12, 343, 349, 553

(56) References Cited

U.S. PATENT DOCUMENTS

| | | | |
|---|---|---|---|
| 4,095,105 A | 6/1978 | Rosenthal | 360/74.2 |
| 4,286,327 A | 8/1981 | Rosenthal et al. | 702/23 |
| 4,379,233 A | 4/1983 | Rosenthal | 250/553 |
| 4,404,642 A | 9/1983 | Rosenthal | 702/85 |
| 4,466,076 A | 8/1984 | Rosenthal | 702/85 |
| 4,480,706 A | 11/1984 | Rosenthal | 177/50 |
| 4,487,278 A | 12/1984 | Rosenthal | 177/25.12 |
| 4,627,008 A | 12/1986 | Rosenthal | 702/23 |
| 4,633,087 A | 12/1986 | Rosenthal et al. | 250/339.12 |
| 4,692,620 A | 9/1987 | Rosenthal | 250/343 |
| 4,734,584 A | 3/1988 | Rosenthal | 250/343 |
| 4,761,552 A | 8/1988 | Rosenthal | 250/252.1 |
| 4,798,955 A | 1/1989 | Rosenthal | 250/341.2 |
| 4,801,804 A | 1/1989 | Rosenthal | 250/341.2 |
| 4,850,365 A | 7/1989 | Rosenthal | 600/473 |
| 4,915,827 A | 4/1990 | Rosenthal | 209/577 |
| 4,928,014 A | 5/1990 | Rosenthal | 250/341.5 |
| 4,969,115 A | 11/1990 | Rosenthal | 702/28 |
| 4,970,671 A | 11/1990 | Rosenthal | 250/252.1 |
| 4,990,772 A | 2/1991 | Rosenthal | 250/252.1 |
| 5,024,533 A * | 6/1991 | Egawa et al. | 374/126 |
| 5,028,787 A | 7/1991 | Rosenthal et al. | 250/339.12 |
| 5,068,536 A | 11/1991 | Rosenthal | 250/341.5 |
| 5,077,476 A | 12/1991 | Rosenthal | 250/339.04 |
| 5,086,229 A | 2/1992 | Rosenthal et al. | 250/339.12 |
| 5,134,302 A | 7/1992 | Rosenthal | 250/504 R |
| 5,204,532 A | 4/1993 | Rosenthal | 250/341.5 |
| 5,218,207 A | 6/1993 | Rosenthal | 250/339.12 |

(List continued on next page.)

OTHER PUBLICATIONS

"Zeltex ZX–50, Portable, Battery–Operated: Near Infrared Whole Grain Analyzer", *Brochure*, 4 pages, 1997.
"Zeltex ZX–101B/C, Portable Octane Analyzer", *Brochure*, 2 pages, 1993.
"Zeltex ZX–550, Near Infrared Portable Food/Cheese Analyzer", *Brochure*, 4 pages, May 2000.
Swedish Institute of Agriculture and Environmental Engineering, Annual Report, 1 page, May 2000.

*Primary Examiner*—N. Le
*Assistant Examiner*—Vincent Q Nguyen
(74) *Attorney, Agent, or Firm*—Rothwell, Figg, Ernst & Manbeck

(57) ABSTRACT

A system for analyzing agricultural products on harvesting equipment includes a test chamber and a near infrared spectrometer disposed within a housing capable of being mounted on the harvesting equipment. A source of near infrared radiation is disposed in the housing adjacent the test chamber so as to emit near infrared radiation into the test chamber, and a near infrared detector is disposed in the housing adjacent the test chamber so as to receive near infrared radiation exiting the test chamber. The spectrometer is mounted on vibration damping elements. A computer controls operation of first and second doors for controlling ingress and egress of product samples from the test chamber and can also be used to process signals from the spectrometer.

31 Claims, 9 Drawing Sheets

U.S. PATENT DOCUMENTS

| | | |
|---|---|---|
| 5,319,200 A | 6/1994 | Rosenthal et al. ........... 250/349 |
| 5,324,979 A | 6/1994 | Rosenthal ............... 250/504 R |
| 5,365,066 A | 11/1994 | Krueger, Jr. et al. ..... 250/341.1 |
| 5,436,455 A | 7/1995 | Rosenthal et al. ..... 250/339.12 |
| 5,438,201 A | 8/1995 | Rosenthal et al. ....... 250/341.1 |
| 5,574,283 A | 11/1996 | Quintana ................. 250/341.1 |
| 5,576,544 A | 11/1996 | Rosenthal ............... 250/341.1 |
| 5,703,364 A | 12/1997 | Rosenthal ............. 250/339.12 |
| 5,751,421 A | 5/1998 | Wright et al. ............... 356/328 |
| 5,957,773 A * | 9/1999 | Olmsted et al. ............. 460/149 |
| 5,991,025 A | 11/1999 | Wright et al. ................ 356/328 |
| 6,064,896 A | 5/2000 | Rosenthal ................... 600/316 |
| 6,066,847 A | 5/2000 | Rosenthal ................ 250/252.1 |
| 6,134,458 A | 10/2000 | Rosenthal ................... 600/310 |
| 6,146,268 A * | 11/2000 | Behnke et al. ................. 460/4 |
| 6,151,517 A | 11/2000 | Honigs et al. ............... 600/316 |
| 2001/0000910 A1 | 5/2001 | Rosenthal et al. ....... 250/341.5 |

\* cited by examiner

SYSTEM AND METHOD FOR ANALYZING AGRICULTURAL PRODUCTS ON HARVESTING EQUIPMENT

BACKGROUND OF THE INVENTION

1. Field of the Invention

The present invention relates to a system and method for determining physical properties of harvested agricultural products on harvesting equipment such as a combine.

2. Description of the Background Art

The conventional method of analyzing agricultural products harvested by a combine involves allowing the agricultural product to fall from the end of the combine elevator into a chute and collecting the agricultural product in a test chamber where load cells determine the weight of the sample, a moisture sensor senses the moisture in the sample, and a sonar device positioned above the chamber determines the volume of the sample. Some of the disadvantages of this approach are that the flow of agricultural product must be interrupted in order to perform an analysis and that it is not possible to determine the other constituents, e.g., protein or oil, of the sample.

Another method of analyzing agricultural products on a combine, exemplified by U.S. Pat. Nos. 5,751,421 and 5,991,025, involves positioning a lamp in the chute or test chamber to irradiate the agricultural product with near-infrared light as it falls from the elevator. Light reflected from the falling product is collected by a sensor and transmitted through a fiber optic bundle to a defraction grating that spreads the reflected light over a photodiode array. By analyzing the strength of the radiation at each photodiode, the amount of constituents in the product sample can be determined. While this approach enhances conventional methods by permitting constituents of a product sample to be measured in a relatively short time period, it is still necessary for the flow of product to be interrupted when the test chamber is full so that other conventional measurements can be made.

There remains a need in the art for an improved method of analyzing agricultural products on harvesting equipment such as a combine.

SUMMARY OF THE INVENTION

Accordingly, it is an object of the present invention to provide a method and apparatus for analyzing agricultural products on harvesting equipment such as a combine that overcomes the disadvantages of the prior art.

A first aspect of the present invention is generally characterized in a system for analyzing agricultural products on harvesting equipment, such as a combine, that creates a flow of harvested agricultural product. The system includes a test chamber and a near infrared spectrometer disposed within a housing capable of being mounted on the harvesting equipment. The test chamber has a first open end adapted to receive a small sample from the flow of harvested agricultural product and a second open end adapted to expel the sample from the test chamber. First and second doors are disposed on opposite sides of the test chamber to control the flow of product into and out of the test chamber. The spectrometer preferably includes a source of near infrared radiation disposed in the housing adjacent the test chamber so as to emit near infrared radiation into the test chamber, and a near infrared detector disposed in the housing adjacent the test chamber so as to receive near infrared radiation exiting the test chamber. The system preferably also includes vibration damping elements that attenuate vehicle vibrations to a level allowing the spectrometer to operate while agricultural product is harvested. The system optionally includes one or more of a computer that operates the first and second doors to control the flow of harvested agricultural product into and out of the test chamber, a fill sensor that indicates when the test chamber is full, at least one temperature probe disposed within the test chamber, a device for maintaining the temperature in the test section within a predetermined range, means for automatically inserting a standard sample into the test chamber at predetermined intervals, and means for adjusting a gap width of the test chamber to accommodate different types of agricultural products.

Another aspect of the present invention is generally characterized in a method of analyzing agricultural products on harvesting equipment, such as a combine, that creates a flow of harvested agricultural product. The method includes the steps of selectively diverting a portion of the harvested agricultural product from the flow created by the harvesting equipment without stopping the flow of product, collecting the diverted portion of the agricultural product in a test section disposed on the harvesting equipment, and analyzing the diverted portion of the agricultural product in the test section using near infrared spectrometry. The analysis is preferably conducted using near infrared transmittance with the sample held stationary within a test chamber disposed in the test section. The method optionally includes one or more of the steps of controlling the flow of product into and out of the test chamber by operating doors disposed on opposite sides of the test chamber, automatically calibrating the spectrometer with a standard sample or no sample in the test chamber at predetermined intervals, mounting the near infrared spectrometer on vibration damping elements to isolate the spectrometer from vibration of the harvesting equipment so that operation of the equipment can continue uninterrupted during the analysis, determining the location where the diverted portion of the agricultural product was harvested using a global positioning system, maintaining the temperature of the near infrared spectrometer within a predetermined range, and controlling a gap width of the test chamber to accommodate different types of agricultural products.

The above and other features and advantages of the present invention will be further understood from the following description of the preferred embodiments thereof, taken in conjunction with the accompanying drawings.

DETAILED DESCRIPTION OF THE PREFERRED EMBODIMENTS

Figure 1:
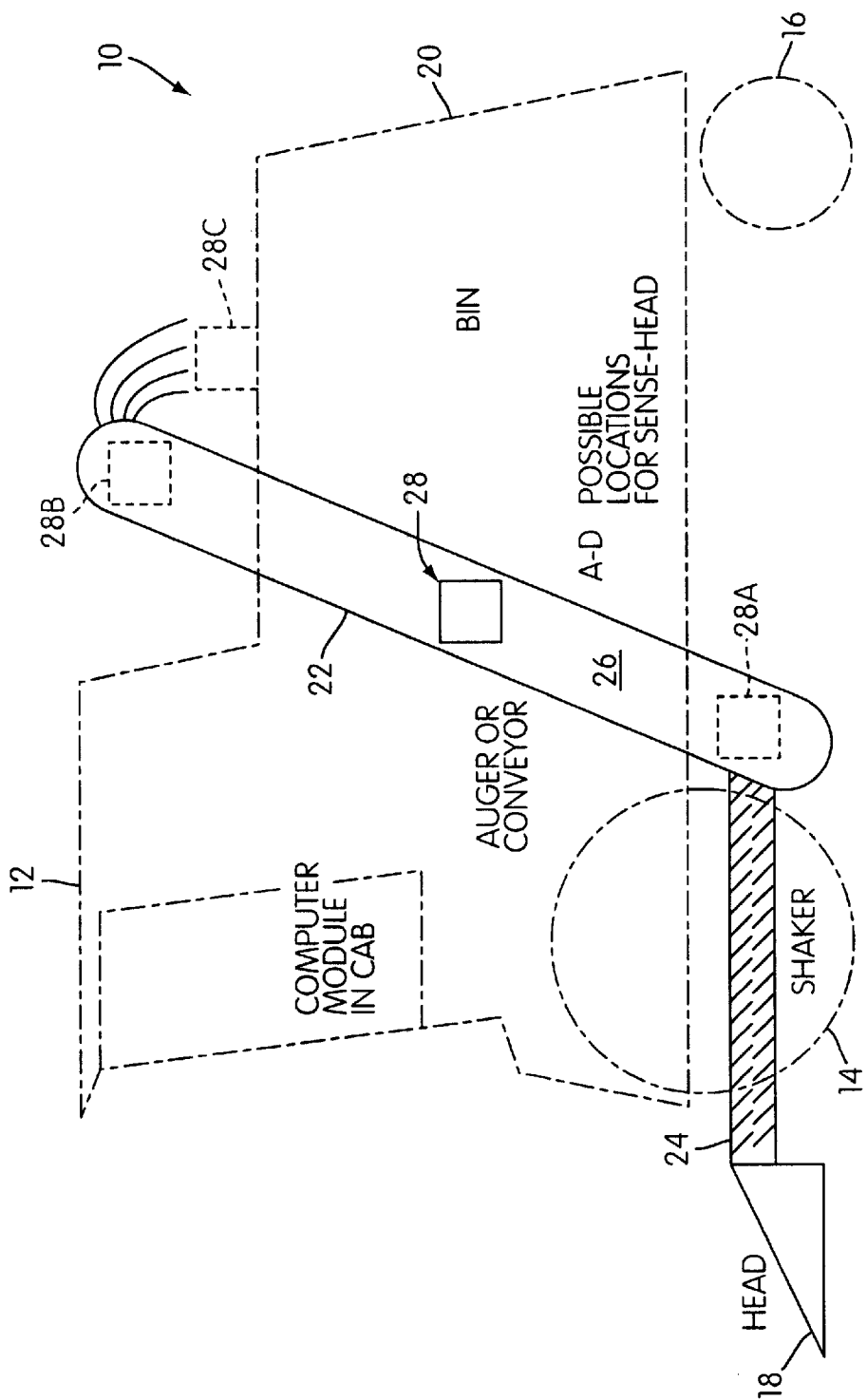
FIG. 1 is a side view of a combine adapted to analyze harvested agricultural products in accordance with the present invention.

FIG. 1 shows a combine 10 adapted to analyze harvested agricultural products in accordance with the present invention. Combine 10 includes a cab 12 mounted on front and rear wheel assemblies 14 and 16, a head 18 mounted forwardly of the cab, a bin 20 mounted rearwardly of the cab, and a sample elevator 22 extending between the head and the bin. Agricultural products harvested by head 18 are passed through a shaker 24 to elevator 22 which moves the agricultural product to bin 20 for collection. Elevator 22 is a tubular structure with at least one side panel 26 that extends upwardly at an angle from a lower end adjacent shaker 24 to an upper end disposed above bin 20. A conveyor (not shown) within the tubular structure receives harvested agricultural products from the shaker via an inlet and moves the products upwardly to an outlet where the products are discharged to fall into the bin. Examples of the types of conveyors that are commonly used include continuous belts and augers. The flow of harvested agricultural product from the head to the bin in the manner described above is referred to herein as the primary or main flow of agricultural product. What has been generally described above is well-known in the art and does not require further explanation for an understanding of the present invention.

In accordance with the present invention, a portion of the agricultural product harvested by the combine is diverted from the main flow of agricultural product into a test section 28 where the diverted portion or sample is collected for near infrared spectrographic analysis. The main flow of agricultural product from the head to the bin can continue uninterrupted as the test sample is diverted and need not be stopped at all during the analysis, thereby obviating one of the major disadvantages of prior art on-combine analysis.

Diversion of the product sample from the flow of agricultural product harvested by the combine can be accomplished anywhere along the main flow of harvested agricultural product at any point past which the agricultural product flows. In the embodiment shown in FIG. 2, for example, a first opening 30 is formed in side panel 26 of elevator 22 adjacent the top (i.e., the upwardly moving) side 31 of a conveyer belt 33 therein to divert a portion of the agricultural product harvested by the combine as it is conveyed upwardly by the elevator. More specifically, as the harvested agricultural product is conveyed upwardly by elevator 22, some of the agricultural product will normally be forced against or slide along the interior surface of elevator side panel 26 such that a portion of the harvested agricultural product will tend to flow out of the elevator through opening 30 in the side panel. The diverted portion of the agricultural product is collected in test section 28 which is disposed outside elevator 22, for example on an outward facing exterior surface of side panel 26 as shown. An optional second opening 32 is shown formed in side panel 26 adjacent the bottom (i.e., the downwardly moving) side 35 of the conveyor belt for return of the sample to the main flow of agricultural product when the sample analysis is complete.

Figure 3:
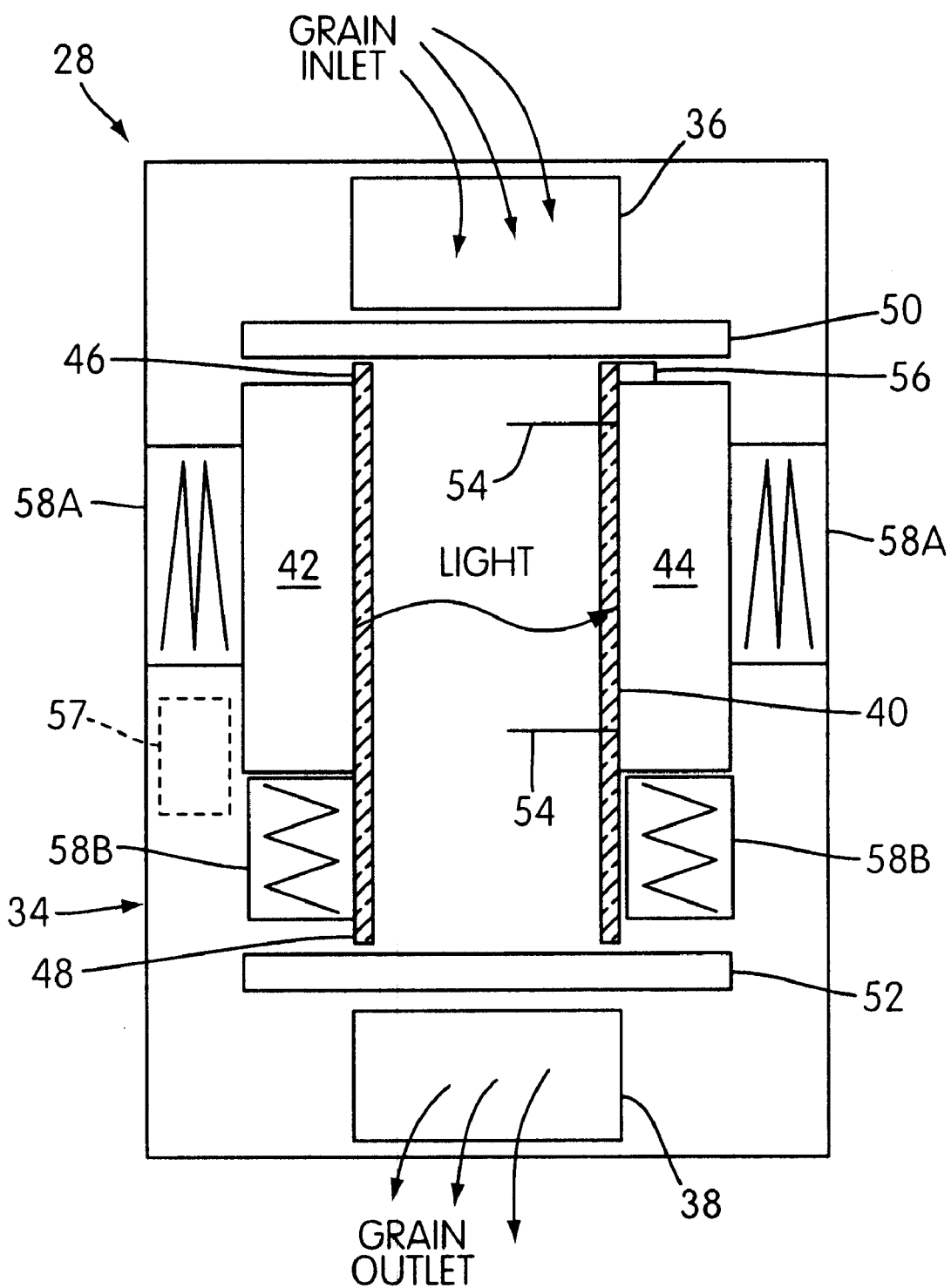
FIG. 3 is a plan view, partly in section, of the test section shown in FIG. 2.

Referring now to FIG. 3, test section 28 is shown including a housing 34 having an inlet portion 36 adapted to communicate with the first opening in the elevator and an outlet portion 38 adapted to communicate with the second opening in the elevator. The test section further includes a test chamber 40 disposed within the housing between the inlet and outlet portions for holding a product sample, and a spectrometer for analyzing the product sample using near infrared radiation, the spectrometer including a source 42 of near infrared radiation positioned in the test section adjacent the test chamber to emit near infrared radiation into the test chamber, and a near infrared detector 44 positioned in the test section on an opposite side of the test chamber to receive near infrared radiation transmitted through the test chamber. Top and bottom ends 46 and 48 of test chamber 40 are open. A first door 50 is disposed between the first opening in the elevator and top end 46 of the test chamber and is movable between an open position allowing agricultural product to flow from the first opening into the test chamber and a closed position preventing the flow of agricultural product into the test chamber. A second door 52 is disposed between bottom end 48 of the test chamber and the second opening in the elevator and is movable between an open position allowing the sample in the test chamber to flow back into the elevator via the second opening and a closed position preventing the sample from flowing out of the test chamber. In the embodiment shown, first and second doors 50 and 52 are mounted on opposite sides of the test chamber 40 adjacent inlet and outlet portions 36 and 38 of the housing, respectively. The doors can be mounted to pivot, slide or otherwise move relative to the chamber and can be controlled by conventional actuators such as pneumatic door cylinders, hydraulic door cylinders, stepper motors, or electromagnetic actuators.

At least a portion of test chamber 40 is formed of a material, such as glass, that is transparent to near infrared radiation. Within the test chamber are one or more probes 54 for measuring the temperature of the sample, for example as disclosed in U.S. Pat. No. 4,404,642, the disclosure of which is incorporated herein by reference. Also disposed in or adjacent the test chamber is a sensor 56 for indicating when the test chamber is full. Sensor 56 can be an optical sensor employing a beam of light that is broken as the product sample reaches the top of the chamber, a limit switch that opens or closes in response to the weight of the sample, a pressure gage, an ultrasonic sensor, or any other type of suitable mechanical, electrical, acoustic or optical sensor. Also shown within test section 28 is an optional temperature control device 57 for maintaining the test section and, thus, the spectrometer, within a predetermined temperature range (e.g., within a few degrees of room temperature) using input from probes 54. Some examples of the types of devices that can be used to control the temperature in the test section include heaters such as resistance wire heaters and coolers such as fans and cooling coils.

Figure 10:
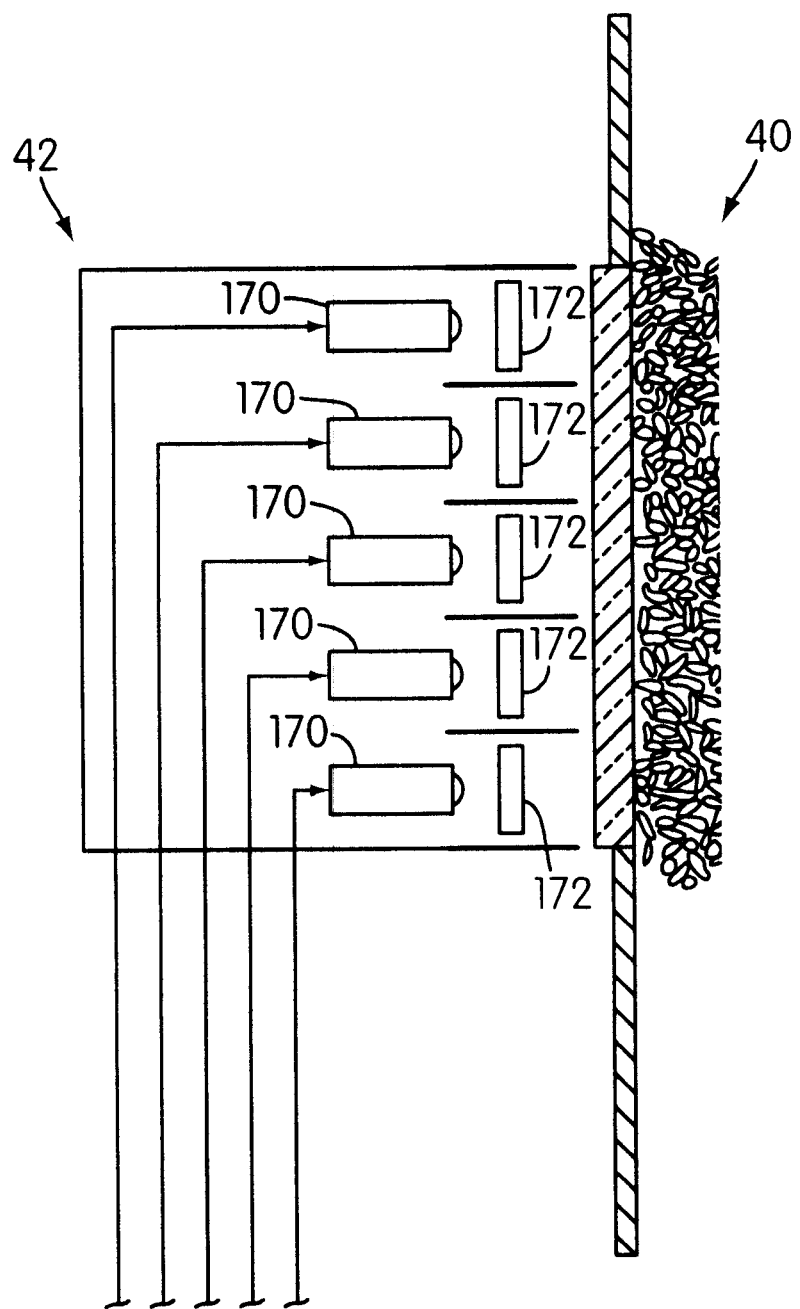
FIG. 10 is a partial side view of a preferred source of near infrared radiation.

The near infrared source and detector within the test section are preferably similar to those used in the near infrared whole grain analyzer commercially available from Zeltex Inc. of Hagerstown, Maryland sold under the-trademark ZX-50 and disclosed in prior patents including U.S. Pat. Nos. 4,286,327 and 4,404,642, the disclosures of which are incorporated herein by reference. The test section can also include or interface with a microprocessor similar to that in the ZX-50. The microprocessor is preferably programmed like that in the ZX-50 to receive data from the detector and calculate results in the form of a percentage of a constituent such as moisture, protein, or oil that can be sent to a display on the test section and/or elsewhere on the combine. The microprocessor can also be programmed to perform other functions such as controlling operation of the doors, controlling operation of any temperature control device, calibrating the system, and communicating with existing electronics on the harvesting equipment. In the ZX-50, and as shown in FIG. 10, the source 42 includes an array of near infrared emitting diodes 170 arranged along one side of the test chamber and narrow bandpass filters 172 disposed between the diodes and the test chamber 40 to produce discrete wavelengths in the near infrared spectrum. Preferably, the wavelengths range from about 800 nm to about 1300 nm. The detector in the ZX-50 is a solid state device positioned on the opposite side of the test chamber to measure the spectra exiting from the sample. It will be appreciated, however, that any source and any detector suitable for near infrared transmittance can be used in the test section and that any suitable microprocessor and programming may be used.

Test section 28 is preferably mounted on vibration damping elements to ensure accurate and reliable readings by isolating the optical components and the test sample from vehicle vibrations that could adversely affect alignment of the optical components relative to each other and the sample during operation. Effective isolation of the test section thus permits an operator to analyze a test sample while continuing to harvest agricultural products. In the embodiment shown in FIG. 3, source 42 and detector 44 are individually mounted on vertical and horizontal vibration damping elements 58B and 58A to provide isolation in two directions. The source and the detector are preferably also individually mounted on a third vibration damping element (not shown) to provide isolation in a third direction perpendicular to the first and second directions. Some examples of the types of vibration damping elements that can be used include pads formed of elastomeric shock absorbing materials, elastic straps, helical springs, leaf springs, pneumatic and hydraulic cylinders, and combinations of the above. Isolation in more than one direction can also be achieved with a single vibration damping element in the form of a boot or sleeve that extends around at least two, and preferably three, sides of the test section and is formed of an elastomeric shock absorbing material. The damping characteristics of the vibration damping elements should be such that any reasonably foreseeable vehicle vibrations and impact loading that may occur when harvesting are attenuated to a level that will not cause the sample to move significantly relative to the optical components of the spectrometer. Since accurate operation of the spectrometer requires precise alignment of the optical components relative to each other and the sample, the amount of attenuation will be chosen to reduce vibration to a level that maintains the critical optical alignment of the components relative to each other and the sample. This level will typically be lower than that needed to protect the components from vibration or shock damage. In other words, greater attenuation of vehicle vibration will typically be needed to stabilize the sample and maintain alignment of the optical components than would customarily be needed to protect the components from vibration damage.

Figure 4:
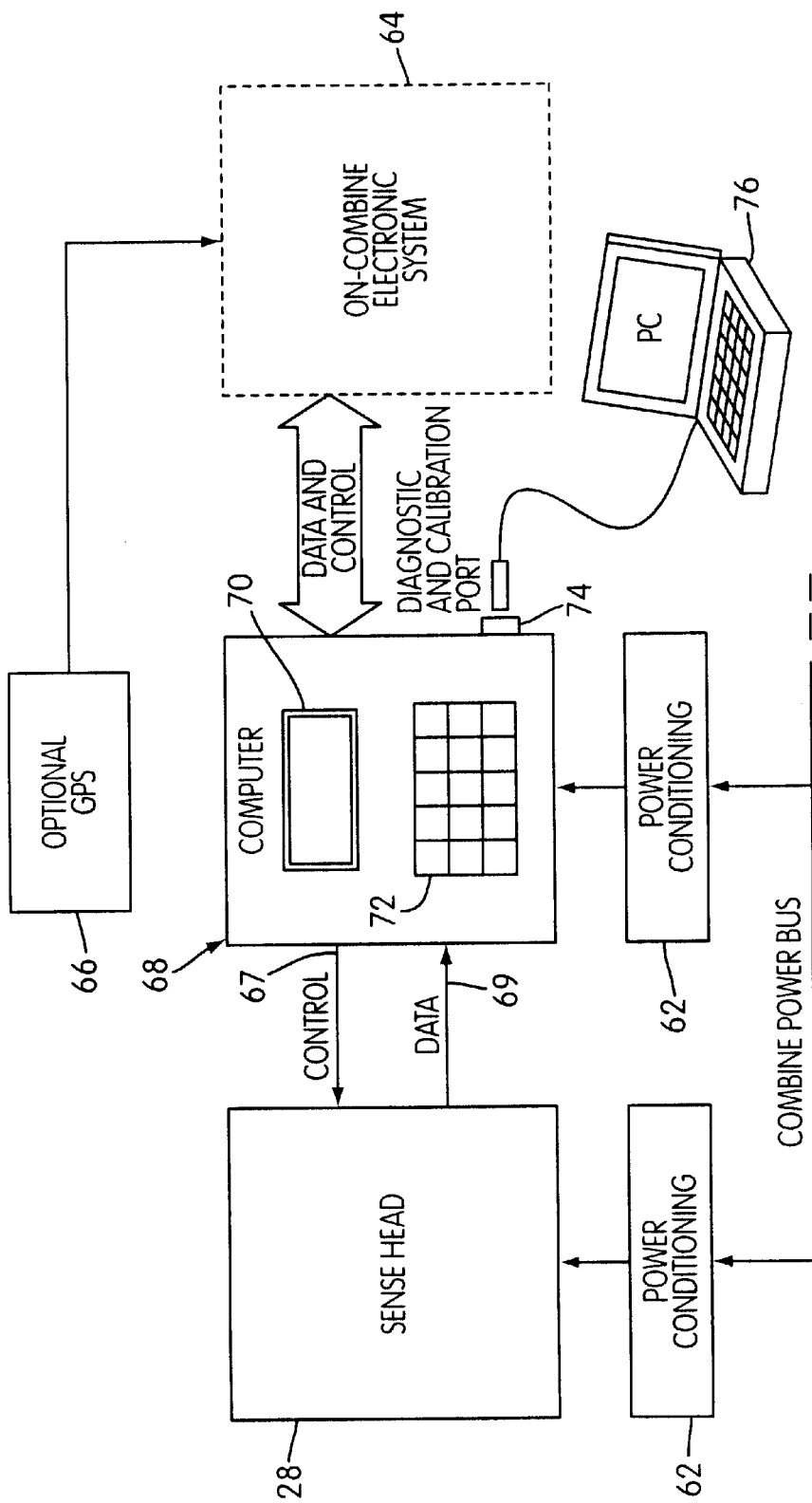
FIG. 4 is a block diagram of a system for analyzing agricultural products utilizing a test section mounted on harvesting equipment in accordance with the present invention.

FIG. 4 is a schematic diagram illustrating how the test section can be integrated with existing electronics on a typical combine to form a system for analyzing harvested agricultural products in accordance with the present invention. The existing electronics include a power bus 60, power conditioning circuitry 62, and an on-board computer 64. The existing electronics may also 20 include an optional global positioning system (GPS) 66. Test section 28 is shown drawing power from the existing combine power bus 60 via power conditioning circuitry 62 and communicating with a computer 68 that is added to the combine electronics as part of the system for analyzing agricultural products in accordance with the present invention. The system computer 68 includes an output port 67 for sending control signals to the test section, an input port 69 for receiving data from the test section, and a central processing unit or microprocessor (not shown) for processing the data from the test section and producing control signals that operate the test section. The system computer can also include at least one of an optional display 70, an optional data input terminal 72 such as a keyboard, and an optional diagnostic/calibration port 74 for interfacing with a portable computing device 76 such as a laptop or any other type of computer or data collection device. Components of system computer 68 can be disposed at different locations on the combine or provided as an integral unit in the test section, the cab, or anywhere else on the combine. Preferably, the system computer components are disposed in the test section. If desired, microprocessors can be located at more than one location so that, for example, some processing functions (e.g., temperature and bias offset compensation) can take place locally in the test section while others (e.g., operation of doors, calculation of constituent percentages, and displaying results) can take place in the cab. The system computer can also communicate with the existing combine computer 64 to receive data relating to position of the combine, control signals indicating a start or stop, etc.

Figure 5:
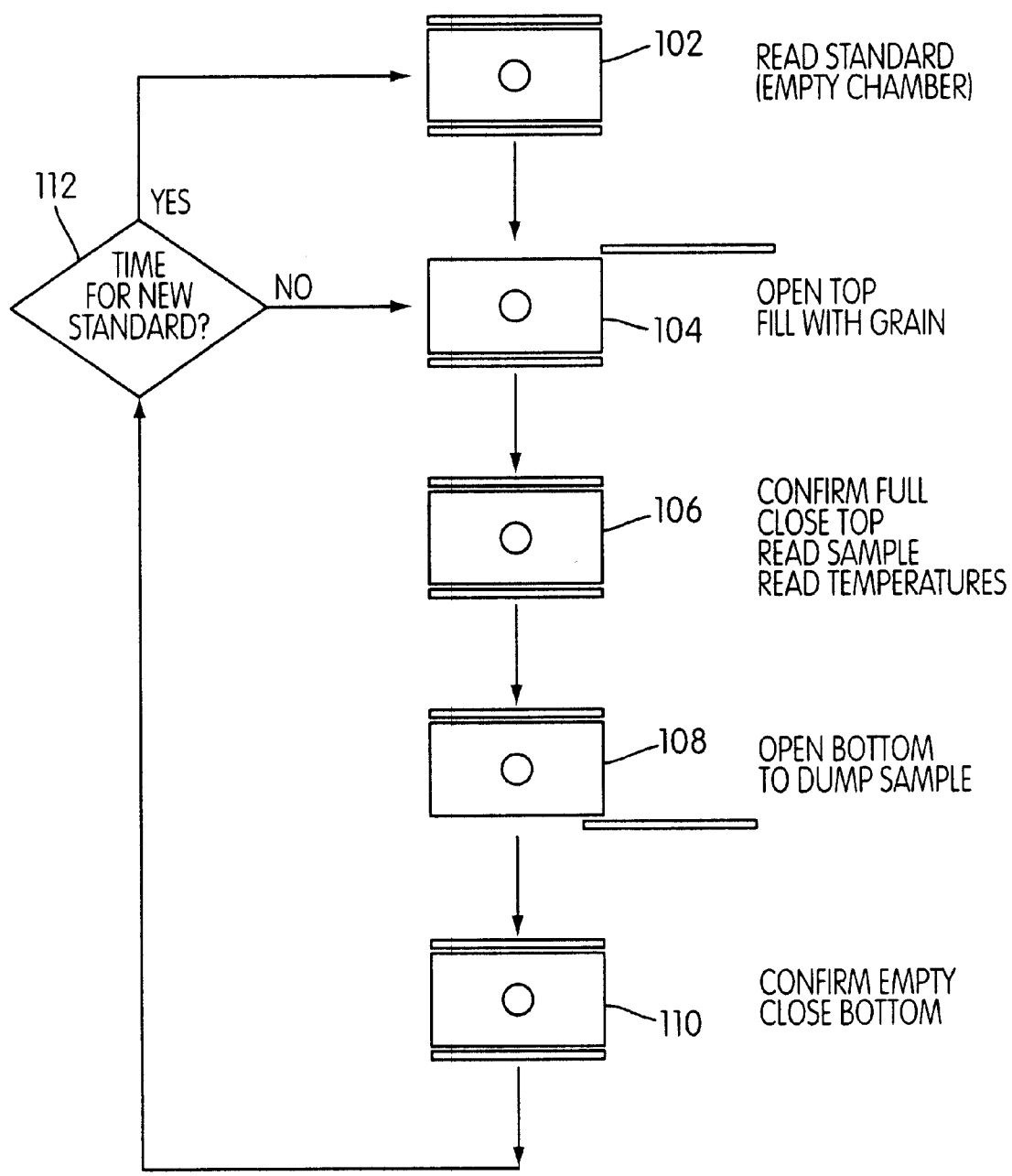
FIG. 5 is a flow chart illustrating a method of analyzing agricultural products utilizing a test section mounted on harvesting equipment in accordance with the present invention.

FIG. 5 is a flow chart illustrating operation of the above described system in accordance with the present invention. The following steps can be performed while the agricultural product is harvested without stopping the combine. In step 102, the analyzer is standardized with doors closed and no sample in the test chamber. By "standardized" is meant adjusted to compensate for drift due to changes in the environment or differences in transmittance of products. One method of standardizing a near infrared analyzer using an empty test chamber is disclosed in U.S. patent application Ser. No. 09/061,893, filed on Apr. 17, 1998, the disclosure of which is incorporated herein by reference. The '893 application describes a method of standardizing the analyzer with an empty test chamber by amplifying the signal generated during standardization using a first gain factor that is lower than the gain factor normally used when analyzing an actual sample. Alternatively, the analyzer can be standardized in the conventional manner using a sealed standardized sample or standard containing a sample of the agricultural product to be analyzed, the sample having been previously analyzed to determine certain parameters of interest that can be used for standardization. Optional use of a standard for standardization obviates the need for multiple gain factors since the transmittance of the standard is selected to be about the same as the actual sample; however, the standard must either be manually placed for standardization or mounted on a device (e.g., a motorized arm, belt or wheel) that automatically inserts the standard into the test chamber for standardization at predetermined intervals or in response to a command entered into the system computer by the operator, and removes the standard from the test chamber once the standardization is complete. This may require the above operation to be modified so that the upper door remains open during standardization to permit the standard to be inserted and removed from the test chamber.

After the analyzer has been standardized, the computer issues a control signal that causes the first or upper door to open (if it is not already open) so that a portion of the main flow of harvested agricultural product is diverted into the test chamber as shown in step 104. The second or lower door remains closed during this time so that the agricultural product diverted from the main flow will collect in the test chamber. A sensor in the test section monitors the fill level of the test chamber and, when the test chamber is full, the sensor sends a signal to the computer indicating that the test chamber is full.

In step 106, the system computer recognizes that the chamber is full and issues a control signal to close the upper door in response thereto. Alternatively, the upper door can be left open (particularly when the product disposed between the test chamber and the door functions to provide an adequate light barrier). The sample contained within the test chamber is then analyzed by causing the light source to emit near infrared light into the sample in the test chamber and using the detector to measure the spectra exiting from the sample. The light energy that enters the sample is scattered and absorbed such that examination of the spectra measured by the detector allows the agricultural product's constituent concentrations, and other parameters, to be determined. Temperature of the sample can also be determined at this time using the probes in the test chamber. Signals from the detector and the probes are sent to the system computer where they are analyzed to determine the parameters of interest (such as percentage moisture, protein, and/or oil) which can be stored for later retrieval, transmitted to a remote location, printed, and/or displayed in the cab for viewing by the combine operator. The results of the analysis can be combined with data from the existing on-board computer such as the time and location where the sample was harvested. The signal from the probes can be used by the computer to compensate for changes in temperature and/or determine whether the temperature in the test section is outside a predetermined range such that heating or cooling of the test section may be needed.

Once the measurements have been taken, the system computer sends a control signal to open the lower door at step 108. This causes the sample to be dumped from the test chamber back into the main flow of agricultural product, onto the ground, or directly into a bin or the like. Alternatively, the sample can be directed into one of a plurality of bins on the basis of protein content, etc. In another alternative, the sample can be bagged for subsequent examination. When the computer receives a signal from the fill sensor confirming that the test chamber is empty, the computer sends a control signal to close the lower door at step 110.

In step 112, the system computer checks if it is time for a new standard and, if so, the above operation is repeated in its entirety. If it is not time for a new standard, the first step 102 is skipped and a control signal is sent to open the upper door to fill the test chamber with a new sample, after which the operation proceeds as described above. The operation described above can be modified so that the first step 102 is preformed with an empty chamber at predetermined intervals (e.g., once every few minutes) while harvesting a particular agricultural product and performed with a standard at predetermined intervals (e.g., once a day) longer than the intervals between standardization with an empty chamber or when preparing to harvest a different type of agricultural product. The steps of filling the test chamber with a sample, taking a reading (i.e., analyzing the sample using near infrared spectrometry), and emptying the sample from the test chamber, can be accomplished in under ten seconds. Since the combine can continue harvesting while a reading is taken, it is possible to take a reading every twenty to thirty feet without stopping. Moreover, since the sampling process does not affect the main flow of product, the combine can continue to operate in a normal manner even if the test system malfunctions.

Figure 6:
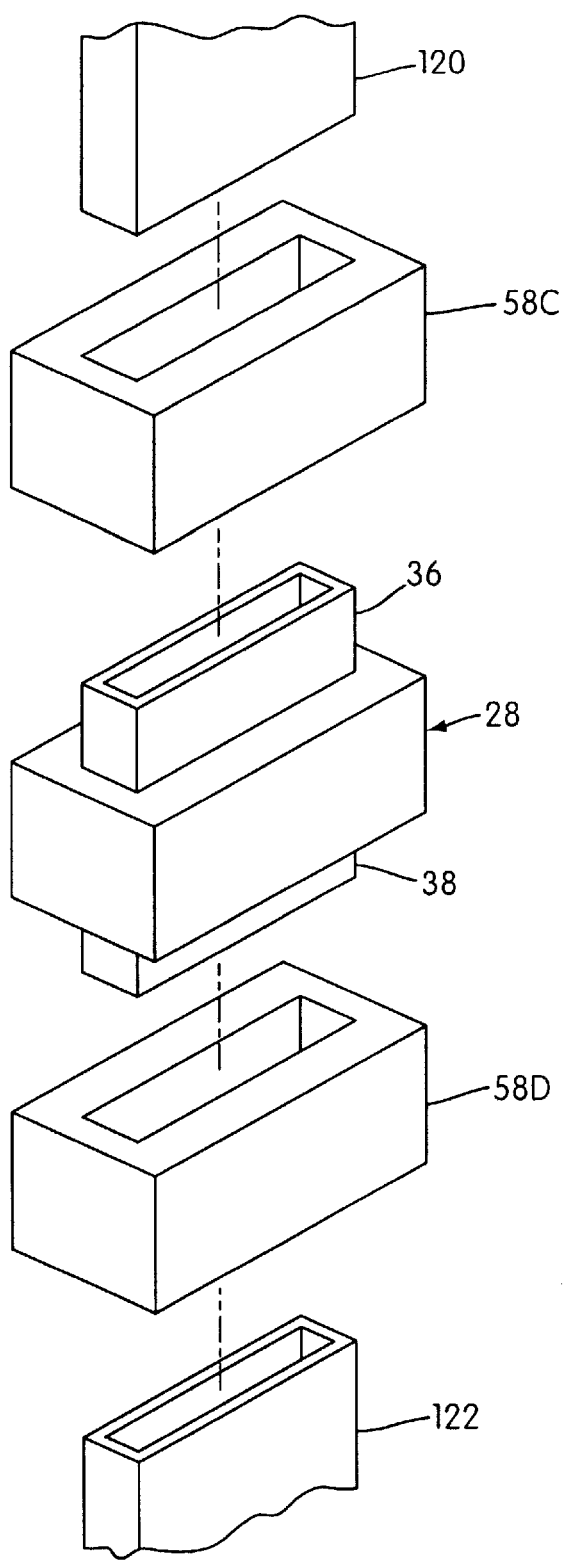
FIG. 6 is a perspective view of another embodiment of a test section according to the present invention.

The test section can be positioned anywhere along the main flow of agricultural product to receive a test sample directly from the main flow, or the test section can be positioned remote from the main flow and receive a test sample indirectly via a conduit, such as a chute, that extends from the main flow to the test section inlet. FIG. 6 illustrates an embodiment wherein test section 28 is disposed remotely of the main flow of agricultural product and receives the test sample via a first conduit 120 leading from an opening in the combine elevator. Test section 28 is identical to that shown and described above; however, vibration isolation is provided by a vibration damping element in the form of an elastomeric coupling or boot 58C disposed between the bottom of the chute and inlet portion 36 of the test section. A second conduit 122 leads from outlet portion 38 of the test section to convey the test sample away from the test chamber and is coupled with the test section via an elastomeric boot 58D similar to the one described above. The test section is thus suspended between vibration damping elements that prevent vehicle vibration in all directions from being imparted to the test section thereby maintaining the precise alignment of the sample relative to the optical components so that the harvesting equipment can continue to operate while a reading is taken.

Figure 2:
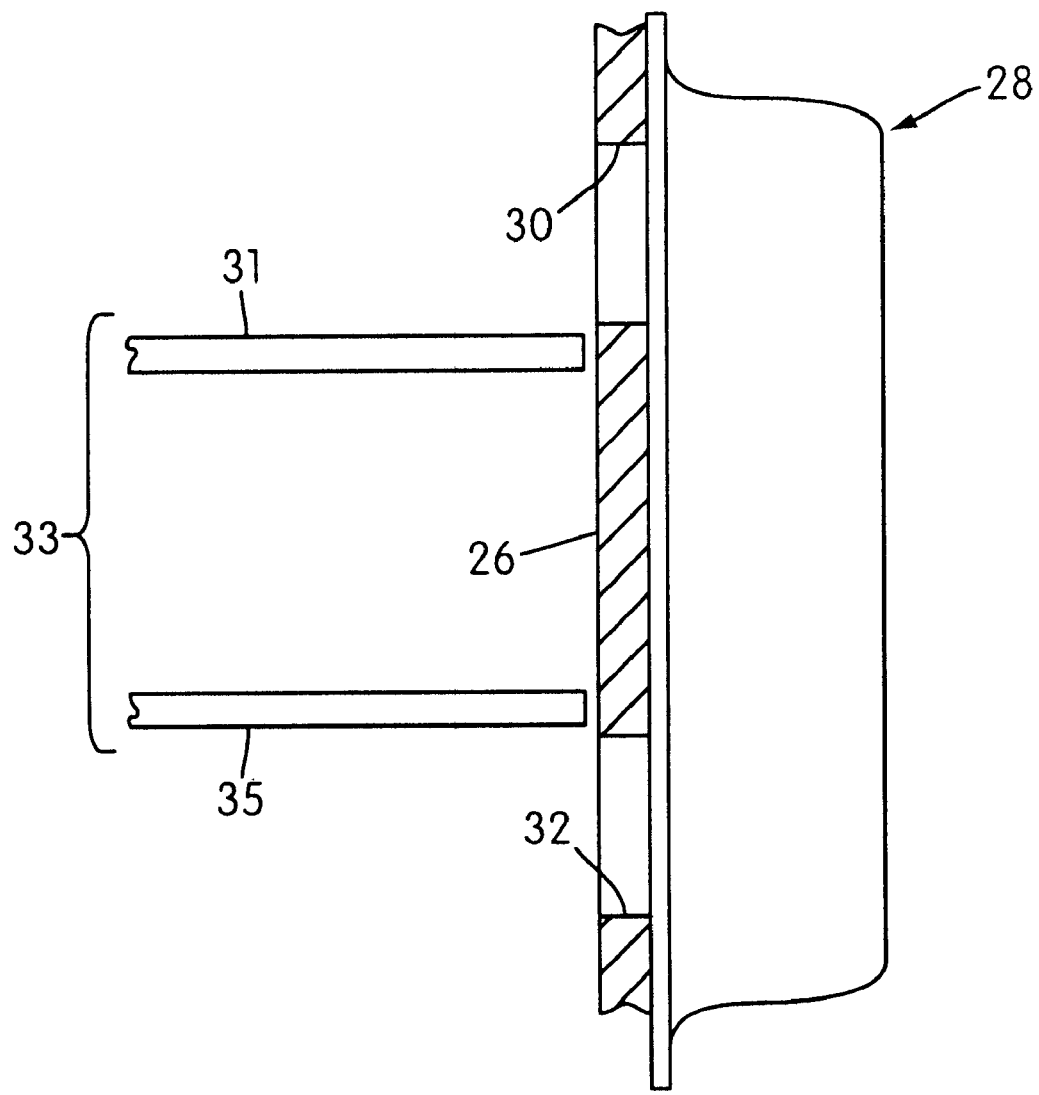
FIG. 2 is a side view, partly in section, of a combine elevator with a test section mounted thereon to analyze harvested agricultural products in accordance with the present invention.

The test section can be placed along the shaker, the elevator, above the bin or anywhere else along the main flow of harvested agricultural product. Examples of alternative locations for the test section described above are shown by broken lines in FIG. 1 at 28A, B and C, respectively. The test section at 28A or 28B is either mounted directly on the elevator over openings formed therein, for example as shown in FIG. 2, or mounted at the end of a conduit leading from openings formed in the elevator at the illustrated locations, for example as shown in FIG. 6. When the test section is placed directly above the bin as shown at 28C, it is preferred that a funnel or hopper (not shown) be positioned above the test section to collect a portion of the agricultural product falling from the elevator.

Figure 7:
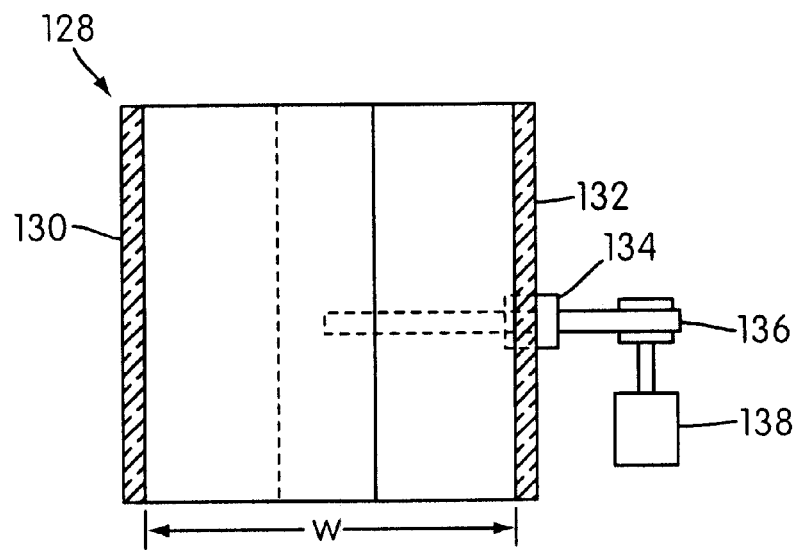
FIG. 7 is a side view, partly in section, of a modification of a test chamber for use in analyzing agricultural products in accordance with the present invention.

The system and method of the present invention permits a wide variety of agricultural products to be analyzed including, but not limited to, grain, forage, oil seed, cereal, and vegetables. Since the transmittance of these agricultural products varies, it has been found that the gap width of the test chamber should be adjusted to match the type of agricultural product being analyzed when near infrared transmittance methods are used. One solution is to manually replace the test chamber with another test chamber of the same design but having a different gap width. Another solution is to manually insert and remove near infrared transparent shims in the test chamber as needed. FIG. 7 illustrates a modification of the test chamber allowing the gap width to be automatically adjusted in response to remote commands from the system computer. The modified test chamber 128 is similar to that described above but is formed of nested chamber halves 130 and 132 allowing telescoping movement of one half of the chamber in relation to the other half of the chamber. Each chamber half includes a pair of parallel side panels connected by a face panel extending perpendicularly between opposed edges of the side panels. Side panels of the inner half 130 fit telescopically within side panels of the outer half 132. The face panels of the respective halves (shown in section) are preferably transparent to near infrared radiation. Outer half 132 is shown mounted on a carrier 134 attached to a belt 136 driven by a motor 138 so that the outer chamber half can be moved relative to the inner chamber half to adjust the gap width w. In a preferred embodiment, the motor can be controlled by entering commands in the system computer and having the computer issue a control signal to the motor causing a change in the gap width. The movable portion of the test chamber can be moved using any type of motive source including, but not limited to, motors, hydraulic cylinders, and pneumatic cylinders. The motive source may act directly on the test chamber or indirectly via belts, arms, screws or other forms of mechanical linkages. Other approaches to make the gap width of the test chamber adjustable include placing a movable wall within the chamber or forming an elastic region (e.g. a bellows) between opposed walls of the chamber so that the walls can move relative to one another.

Figure 8:
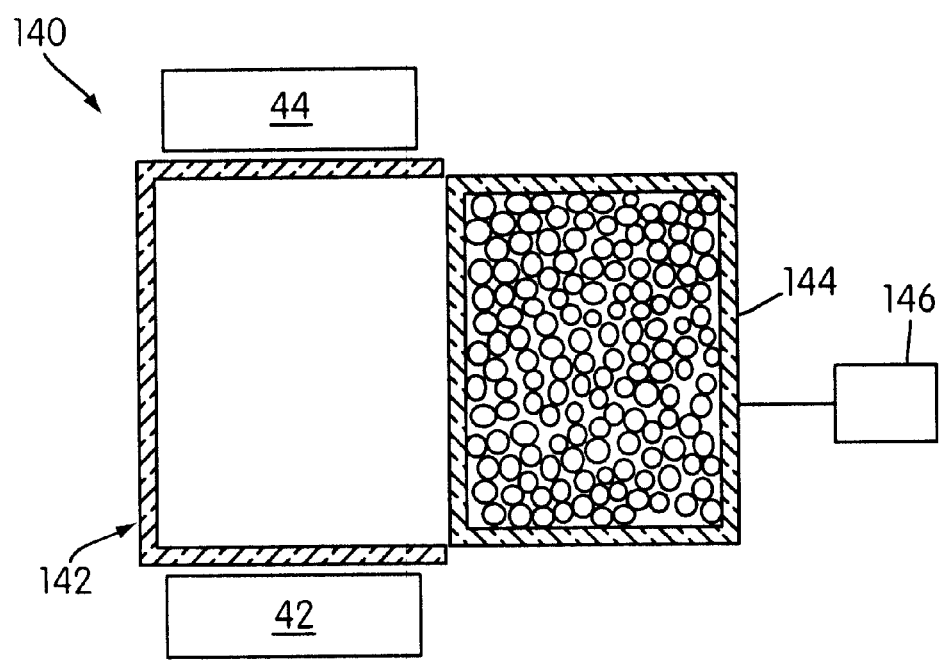
FIG. 8 is top view, partly in section, of another modification of a test chamber for use in analyzing agricultural products in accordance with the present invention.

FIG. 8 illustrates a modification of the test section permitting a standard sample to be automatically inserted into and removed from the test chamber. The modified test section 140 is similar to test section 28 described above, however, a side of test chamber 142 not facing source 42 or detector 44 is open and a standard sample 144 is mounted for movement between an inserted position (not shown) within the test chamber for calibration and a removed position (shown) adjacent the open side of the test chamber allowing an actual product sample to fill the chamber. Test chamber 142 is in all other respects similar to test chamber 40. Alternatively, the standard sample can be positioned for insertion into one of the open ends of the test chamber. Standard sample 144 is preferably a sealed container formed of a near infrared transparent material and filled with an agricultural product of interest or a simulated sample made out of a material that preferably does not vary with time or temperature. The standard sample can be moved into and out of the test chamber by any type of motive source 146 including, but not limited to, motors, hydraulic cylinders, and pneumatic cylinders. The motive source can act directly on the standard sample or indirectly via belts, arms screws or other forms of mechanical linkages.

Figure 9:
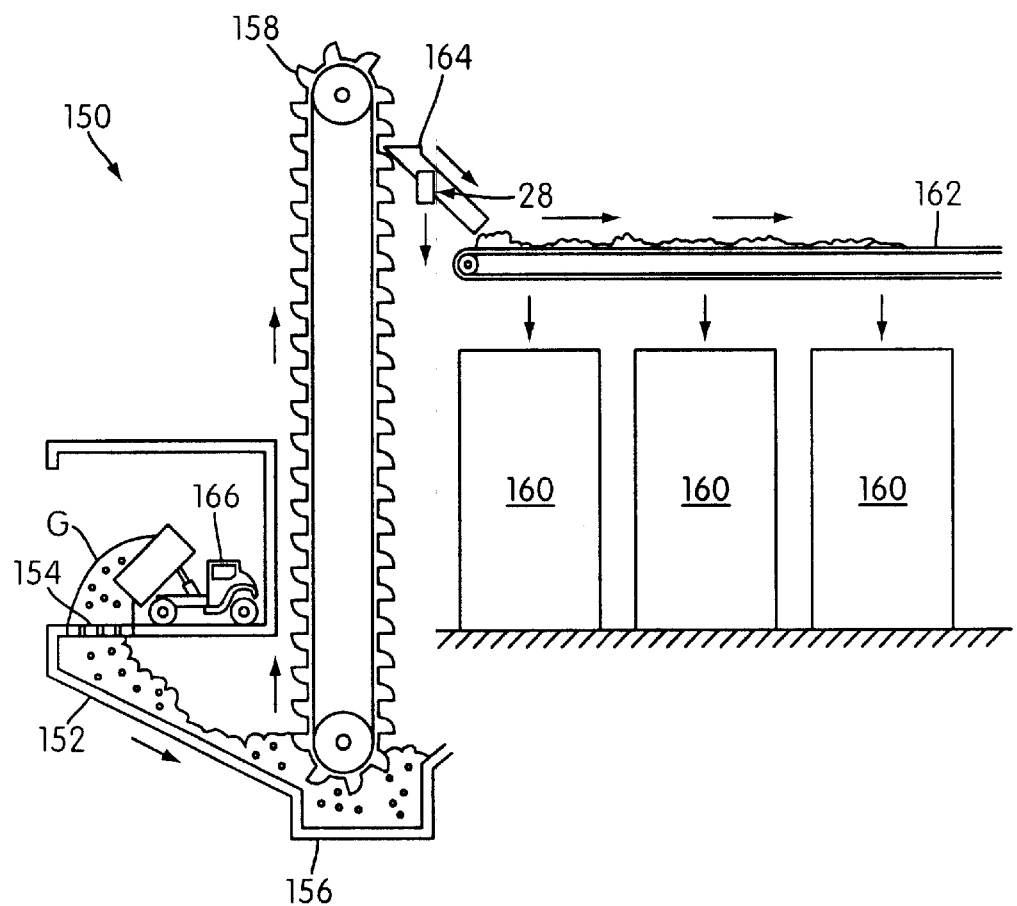
FIG. 9 is a schematic diagram of a conventional grain elevator with a test section mounted thereon to analyze harvested agricultural products in accordance with the present invention.

The test section can be mounted on a combine, a chopper, a hay bailer or any other type of harvesting equipment that creates a flow of harvested agricultural products. For example, in FIG. 9, a test section 28 is shown mounted on harvesting equipment in the form of a grain elevator 150. While a particular type of grain elevator is shown, it will be appreciated that the test section can be mounted along the flow of grain in any type of grain elevator. The grain elevator 150 shown in FIG. 9 includes a large pit 152 covered by a grate 154 for receiving a load of grain. The large pit 156, commonly referred to as the "dump" pit, defines a downwardly sloping path to a lower pit, commonly referred to as the "boot." The grain elevator further includes a vertical carousel 158, commonly referred to as the "leg," that includes a continuous belt carrying a plurality of cups or buckets extending upwardly from the boot, one or more silos or bins 160, and a conveyor belt 162 that extends from the leg to the bin(s).

The test section 28 is shown disposed on a conduit 164 between the top of the leg 158 and the conveyor belt 162 to receive a portion of the grain falling from the leg; however, the test section can be disposed anywhere along the flow of grain in the elevator. For example, the test section could be placed along the dump pit, the leg, the conduit, the conveyer belt, or the bins.

In operation, a truck 166 loaded with grain G drives into the elevator 150 adjacent the grate 154 and dumps the grain into the dump pit 152 through the grate. Grain slides from the dump pit 152 to the boot 156 where it is picked-up by cups on the rotating belt of the leg 158 and carried to the top of the leg. As the belt goes over the top of the leg 158 and turns to go back down, the cups turn upside down and dump the grain into the conduit 164 which conveys the grain onto the conveyer belt 162. A portion of the grain flowing through the conduit 164 is diverted through an opening therein into the test section 28 where it is analyzed and expelled as described above in connection with a combine. If the elevator includes a plurality of bins, the results of the analysis by the test section can be used to determine into which bin the conveyor will deposit the grain. The bins can thus be categorized by moisture content, type of grain, protein, or any other characteristic. The test section can also be positioned to analyze grain as it is dispensed from a bin. Such features help maximize profit when selling the grain.

While the invention has been described in detail above, the invention is not intended to be limited to the specific embodiments as described. It is evident that those skilled in the art may now make numerous uses and modifications of and departures from the specific embodiments described herein without departing from the inventive concepts. For example, while use of near infrared transmittance has been disclosed, it will be appreciated that certain constituents of the sample can be analyzed using near infrared reflectance by rearranging the detector to receive light reflected from the sample. The analysis described above can be conducted while the harvesting equipment continues to move the agricultural product or when the equipment has stopped moving the agricultural product. Heating and/or cooling devices can be provided in the test section to maintain the temperature within a predetermined range (e.g., within a few degrees of room temperature) to increase accuracy by ensuring that the optics remain calibrated. First and second doors are preferably disposed within the housing at opposite ends of the test chamber as shown and described above; however, if the test section is disposed remotely of the main flow of agricultural product, the first door can be positioned adjacent the flow of agricultural product. Alternatively, the first door can be disposed adjacent the test section and a third door provided adjacent the flow of agricultural product to prevent a build-up of product above the first door while a sample is being analyzed.

What is claimed is:

1. A system for analyzing agricultural products on harvesting equipment that creates a flow of harvested agricultural product, said system comprising:

a housing capable of being mounted on the harvesting equipment;

a test chamber disposed within said housing and having a first open end adapted to receive a sample from the flow of harvested agricultural product and a second open end adapted to allow the sample to exit from the test chamber;

a first door disposed between the flow of harvested agricultural product and said first open end;

a second door disposed adjacent said second open end;

a source of near infrared radiation disposed in said housing adjacent said test chamber so as to emit near infrared radiation into said test chamber, wherein said source comprises infrared emitting diodes and a narrow bandpass filter disposed between each of said diodes and said test chamber;

a near infrared detector disposed in said housing adjacent said test chamber so as to receive near infrared radiation exiting said test chamber; and a computer in signal communication with said first and second doors, said source, and said detector, wherein said computer is programmed to:

(a) cause movement of said first door between open and closed positions to control the flow of harvested agricultural product into said test chamber;

(b) to cause movement of said second door between open and closed positions to control the flow of harvested agricultural product from said test chamber;

(c) to open said first door when said second door is closed in order to collect a sample for analysis in said test chamber;

(d) to close said first door when there is a prescribed amount of agricultural product in said test chamber; and (e) to receive data from said detector for analysis while said second door is closed and after the prescribed amount of agricultural product is collected in said test chamber and to open said second door to expel the sample when the analysis is complete.

2. The system of claim 1, further comprising a vibration damping element, wherein at least one of said source and said detector is mounted on said vibration damping element to attenuate equipment vibration in at least one direction.

3. The system of claim 1, further comprising a fill sensor indicating when said test chamber is full, wherein said computer is programmed to close said first door when said fill sensor indicates that said test chamber is full.

4. The system of claim 1, wherein said computer is programmed to retrieve data indicating a position of the harvesting equipment from a global positioning system and relate the position data to specific sample data received from said detector.

5. The system of claim 1, further comprising a temperature sensor in said test chamber.

6. The system of claim 1, further comprising at least one of a heating device and a cooling device in said housing for maintaining said source and said detector at a desired temperature.

7. The system of claim 1, wherein the harvesting equipment is a combine having a tubular elevator with at least one opening formed in a side thereof, and wherein said housing is adapted to be mounted on said elevator adjacent the opening in the elevator such that a portion of the agricultural product flows through the opening into said first open end of said test chamber.

8. The system of claim 1, wherein said computer is programmed to periodically calibrate said system by closing said first and second doors with no sample in said test chamber.

9. The system of claim 8, further comprising a standard sample configured for movement between a position in said test chamber and outside said test chamber, wherein said computer is programmed to periodically calibrate said system with said standard sample by causing said standard sample to move into said test chamber for analysis.

10. The system of claim 1, further comprising a plurality of vibration damping elements, wherein at least one of said source and said detector is mounted on said plurality of vibration damping elements to attenuate equipment vibration in a plurality of directions perpendicular to one another.

11. The system of claim 10, wherein said housing is suspended between a pair of said vibration damping elements.

12. The system of claim 11, further comprising a first conduit adapted to extend between the flow of agricultural product created by the equipment and said housing.

13. The system of claim 12, wherein one of said vibration damping elements is an elastomeric boot coupling said housing with said first conduit.

14. The system of claim 12, further comprising a second conduit adapted to extend from said outlet portion of said housing.

15. The system of claim 14, wherein one of said vibration damping elements is an elastomeric boot coupling said housing with said first conduit and another of said vibration damping elements is an elastomeric boot coupling said housing with said second conduit.

16. A method of analyzing agricultural products on harvesting equipment that creates a main flow of harvested agricultural product, said method comprising the steps of:

selectively diverting a portion of the harvested agricultural product from the main flow of harvested agricultural product without stopping the main flow of agricultural product;

collecting and holding the diverted portion of the agricultural product in a test section disposed on the harvesting equipment; and analyzing the diverted portion of the agricultural product in the test section using near infrared spectrometry while the diverted portion is held stationary in the test section.

17. The method of claim 16, wherein the test section includes a test chamber configured to hold the diverted portion of the harvested agricultural product in a stationary position for analysis, and wherein said collecting step includes the step of opening a door disposed between the test chamber and the flow of harvested agricultural product.

18. The method of claim 17, further comprising the step of closing the door when the test chamber is full.

19. The method of claim 18, further comprising the step of emptying the test section after analyzing the diverted portion of the agricultural product in the test section.

20. The method of claim 19, wherein said emptying step includes opening a door disposed at the bottom of the test chamber.

21. The method of claim 20, wherein said emptying step includes the step of returning the diverted portion to the flow of harvested agricultural product created by the harvesting equipment.

22. The method of claim 16, further comprising the step of automatically calibrating the spectrometer with the test chamber empty at predetermined intervals.

23. The method of claim 22, further comprising the step of automatically calibrating the spectrometer for bias error with a standard sample in the test chamber at predetermined intervals.

24. The method of claim 23, wherein the intervals between said bias calibration steps are greater than the intervals between said empty test chamber calibration steps.

25. The method of claim 16, further comprising the steps of determining the location where the diverted portion of the agricultural product was harvested using a global positioning system.

26. The method of claim 16, further comprising the step of maintaining the temperature of the near infrared spectrometer within a predetermined range.

27. The method of claim 16, further comprising the step of mounting the near infrared spectrometer on vibration damping elements to isolate the sample from vibration of the harvesting equipment.

28. The method of claim 16, wherein said analyzing step includes adjusting a gap width of the test chamber to accommodate more than one type of agricultural product.

29. The method of claim 16, further comprising the step of mounting the test section on a combine.

30. The method of claim 16, further comprising the step of mounting the test section in a grain elevator.

31. The method of claim 30, wherein the grain elevator includes a plurality of bins, and further comprising the step of depositing the harvested agricultural product into a specific bin based on a characteristic of the agricultural product determined during the analyzing step.

* * * * *